US006668625B2

(12) United States Patent
Weis et al.

(10) Patent No.: US 6,668,625 B2
(45) Date of Patent: Dec. 30, 2003

(54) MEASUREMENT OF THE LEVEL OF SETTLED PARTICLES WITHIN A FLUID VESSEL

(75) Inventors: Frank G. Weis, Kansas City, MO (US); Robert Davis, Jr., Peculiar, MO (US)

(73) Assignee: Smith & Loveless, Inc., Lenexa, KS (US)

( * ) Notice: Subject to any disclaimer, the term of this patent is extended or adjusted under 35 U.S.C. 154(b) by 53 days.

(21) Appl. No.: 10/014,116

(22) Filed: Oct. 26, 2001

(65) Prior Publication Data

US 2003/0079527 A1 May 1, 2003

(51) Int. Cl.[7] .......................... G01N 33/18; G01N 7/00
(52) U.S. Cl. .................... 73/61.78; 73/61.78; 73/61.63; 73/61.71
(58) Field of Search ........................ 73/61.78, 61.63, 73/67.71

(56) References Cited

U.S. PATENT DOCUMENTS

| 3,941,698 A | 3/1976 | Weis |
| 4,107,038 A | 8/1978 | Weis |
| 4,270,676 A | 6/1981 | Green |
| 4,519,907 A | 5/1985 | Rooney |
| 4,759,854 A | 7/1988 | Wilson |
| 4,767,532 A | 8/1988 | Weis |
| 5,641,397 A | * 6/1997 | Grienberger ................. 210/97 |

FOREIGN PATENT DOCUMENTS

JP 61161423 A * 7/1986 ............. G01F/1/74

* cited by examiner

*Primary Examiner*—Hezron Williams
*Assistant Examiner*—André K. Jackson
(74) *Attorney, Agent, or Firm*—Wood, Phillips, Katz, Clark & Mortimer

(57) ABSTRACT

A system and method of measuring a level of settled particles in a fluid-containing vessel includes the steps of fluidizing particles from a position below the settled level of particles, and measuring a static pressure of liquid within the vessel at a position in the vessel below the settled level of particles. The fluidized static pressure is correlated to a level of settled particles within the vessel using an experimentally determined relationship. The apparatus includes an inlet pipe into the vessel at a position below the settled level of particles, and a pump which recirculates liquid from the vessel above the submerged level of particles, remote from the settled level of particles, and a static pressure instrument connected to the inlet pipe. A solids pump can be activated to remove settled particles from the vessel, the operation of the pump being controlled by the measured level of settled particles.

13 Claims, 2 Drawing Sheets

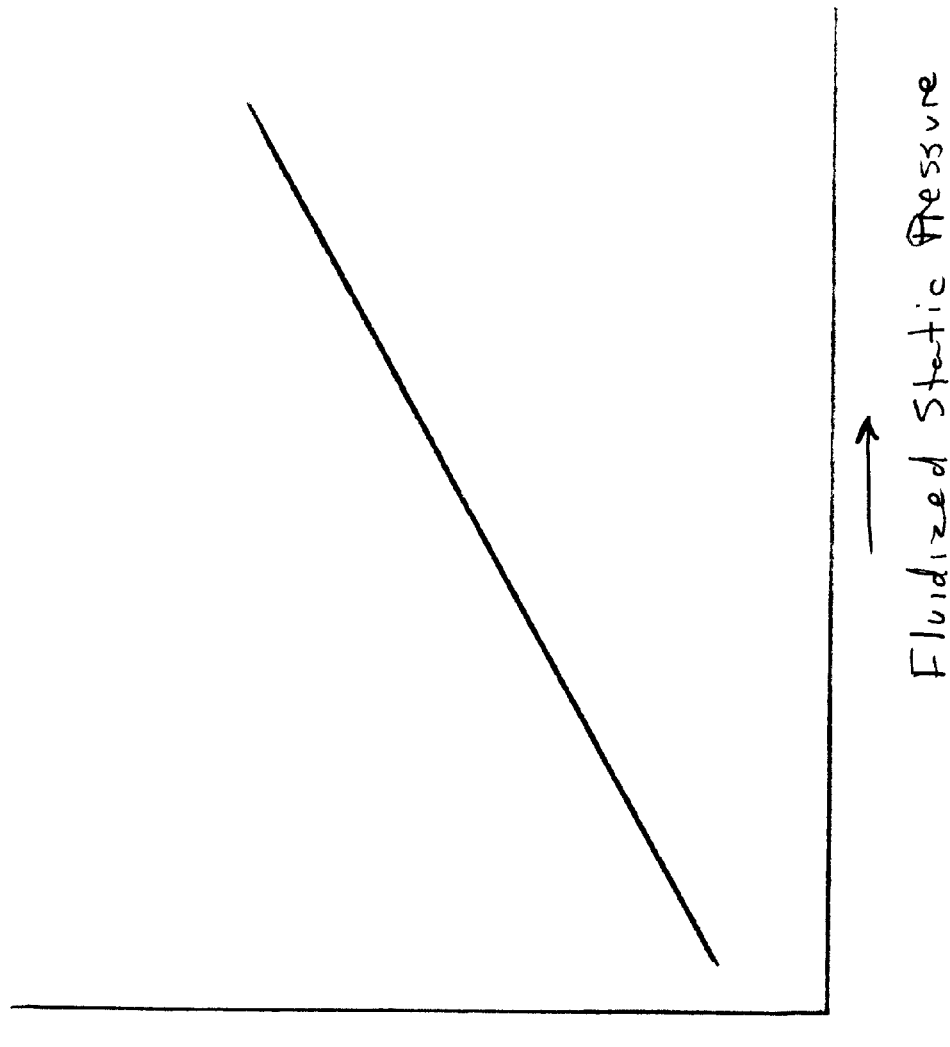

MEASUREMENT OF THE LEVEL OF SETTLED PARTICLES WITHIN A FLUID VESSEL

TECHNICAL FIELD OF THE INVENTION

The present invention relates to process measurement techniques and apparatus. Particularly, the invention relates to a measurement technique and apparatus for determining the level of settled particles in a fluid reservoir or process vessel.

BACKGROUND OF THE INVENTION

In liquid treating plants, it is sometimes desired to measure the level of settled grit or sand in a fluid within a vessel. The level of grit or sand in a liquid within a vessel has been measured typically in two ways: by measuring the distance from the surface of the liquid to the surface of the grit, or by weighing the liquid and grit to determine the percentage of grit by the added weight.

The first method suffers the drawback that, in many process vessels, there is no clear passage from the surface of the liquid to the surface of the grit or sand to make a direct measurement. The second method suffers the drawback that, in a large process facility, the weighing of a large vessel is not always possible or practical.

The present inventors have recognized the desirability of providing an effective method and apparatus for measuring the level of grit or sand in a fluid within a fluid vessel or reservoir. The present inventors have recognized the desirability of providing a method and apparatus for measuring the level of grit or sand in a fluid within a vessel or reservoir that does not require a clear passage down to the surface of the sand or grit or a weighing of the vessel or reservoir to determine to level of sand or grit therein.

SUMMARY OF THE INVENTION

The invention provides a method and apparatus for measuring the level of particles, such as sand or grit, in a liquid within a vessel or reservoir. The method and apparatus are simple and cost effectively incorporated into the vessel or reservoir.

Settled particles, such as grit or sand, maintain a submerged level within a vessel by a mechanism wherein the particles support themselves on the bottom of the vessel with individual grains resting on other individual grains. The settled particles result in an angle of repose of the particles. Accordingly, the pressure exerted by the particles is not equal in every direction. The particles do not, in fact, exert pressure in the same sense that a liquid exerts pressure. The particles are supported by the bottom of the vessel, although some lateral force due to the weight is exerted against the side of the vessel. The liquid contained within the vessel surrounds the particles and penetrates the void between the particles. Fluid pressure measured by a conventional pressure measuring device at a level of the vessel below the submerged level of particles is a measure only of the liquid pressure in the vessel. Thus, a static fluid pressure reading at a bottom of the vessel, measured in a conventional manner, will not be useful to determine the level of grit within the vessel.

The present invention provides a technique for using a static fluid pressure reading to determine the level of settled particles within the vessel. The method of the invention includes the steps of:

providing a vessel containing a volume of liquid defining a liquid level, and a volume of particles settled to the bottom of the volume of liquid;

establishing a position within the vessel below the submerged level of particles;

fluidizing the particles above the position;

measuring a fluidized static pressure of the liquid including the fluidized particles; and comparing the fluidized static pressure with an experimentally established relationship between level of settled particles and fluidized static pressure.

The relationship of fluidized static pressure is proportional to the level of the settled particles within the vessel above the level of the position. The correlation or relationship of the level of settled particles and the fluidized static pressure for the particular liquid and particles is pre-established experimentally.

The fluidizing of the particles can be done continuously or intermittently. A static measurement of the fluid in a non-fluidized region of the vessel, or at the fluidizing inlet before fluidizing, can be used to establish a datum for non-fluidized static pressure with the vessel. This datum is influenced by the density of the liquid and entrained particles within the vessel as well as the liquid level within the vessel. The datum will influence the correlation between fluidized particles and the calculated level of settled particles within the vessel.

The apparatus for performing the method includes a vessel for holding the liquid and the submerged particles, a pipe or line for delivering fluid into the vessel below the submerged level of particles, and a static pressure measuring instrument located at the position. The static pressure measuring instrument is configured to measure static pressure in the vessel at the position. The line for delivering fluid can be from a separate source of pressurized fluid such as pressurized water (city water), or from liquid re-circulated from the vessel. The line can be connected at an inlet end thereof to the vessel at a position above the submerged level of particles, preferably remote from the pressure measuring position. The apparatus can include a pump for delivering the fluid under pressure through the line and into the vessel. The pressure measuring device can be a pressure gauge connected to the line, close to the vessel.

As a further development, the pressure measuring instrument can be a pressure switch that is signal-connected to a solids pump. The solid pump can be operated intermittently as needed to control the level of particles in a vessel, responsive to the pressure measuring instrument.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 2 is a graphical depiction of fluidized static pressure relationship to grit level in a vessel.

DETAILED DESCRIPTION OF THE PREFERRED EMBODIMENTS

Figure 1:
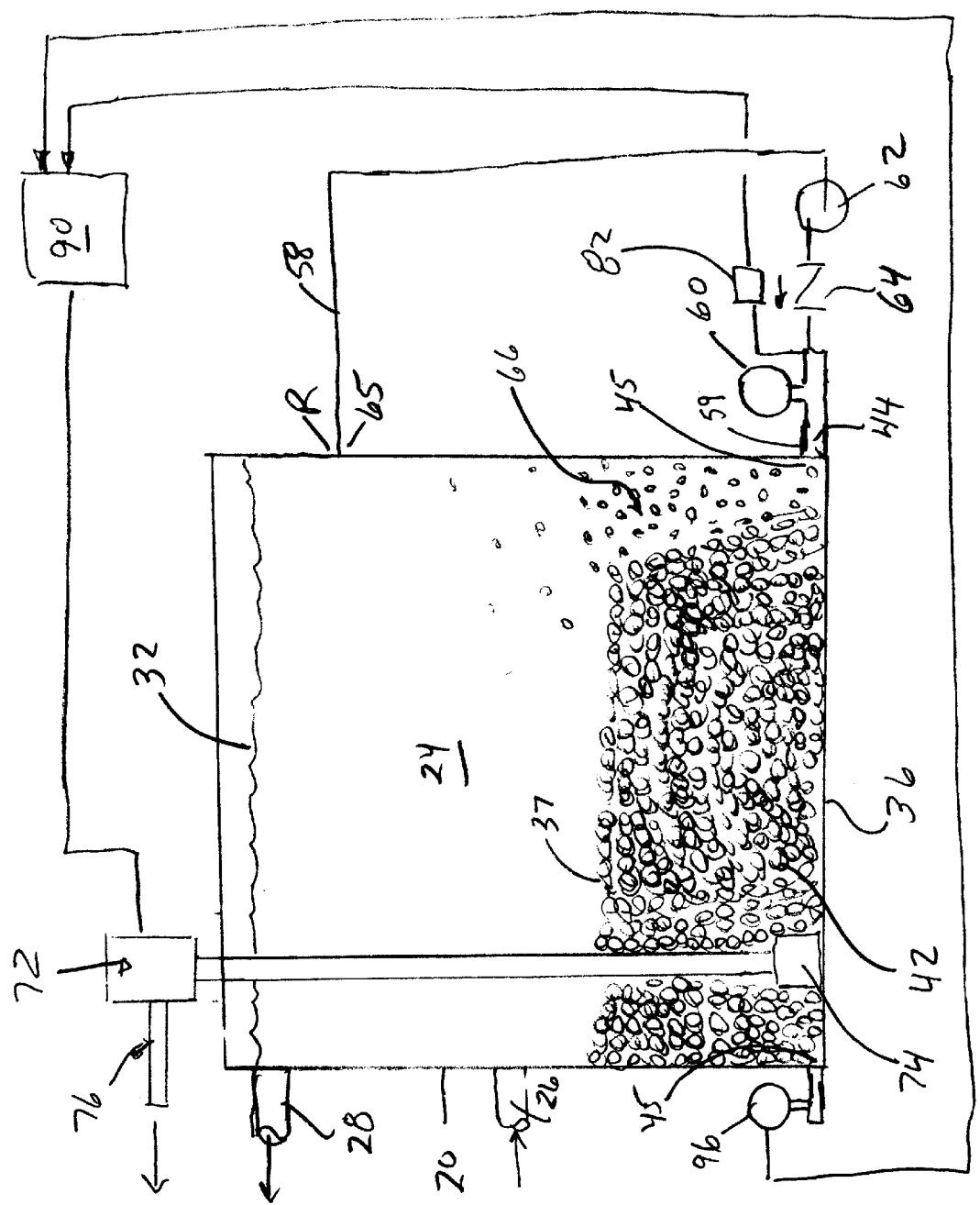
FIG. 1 is a schematic sectional view of a measuring system according to the invention.

While this invention is susceptible of embodiment in many different forms, there are shown in the drawings, and will be described herein in detail specific embodiments thereof with the understanding that the present disclosure is to be considered as an exemplification of the principles of the invention and is not intended to limit the invention to the specific embodiments illustrated.

FIG. 1 illustrates a system 10 of the invention which is effective to determine the level of particles within a vessel. The system includes a vessel 20 containing a liquid 24 such as water, particularly sewage. The vessel includes a process liquid inlet 26 and an outlet 28. The liquid 24 maintains a level 32 within the vessel. The vessel includes a bottom 36. A quantity of particles 42, the particles settled within the liquid 24, rests on the bottom 36 of the vessel 20. The particles 42 can be sand, grit or other materials that settle within the liquid 24. The particles establish a submerged level 37 within the liquid 24.

The vessel can be a grit extractor such as disclosed in U.S. Pat. Nos. 4,767,532; 4,107,038 or 3,941,698, herein incorporated by reference. The vessel can be the grit storage chamber of the grit extractor as disclosed in the aforementioned patents.

A fluidizing liquid inlet 44, such as a vessel nozzle or a connection 59 to the vessel wall enters the vessel 20 at a position 45 below the level 37. A line or pipe 58 is connected to the inlet 44. A static pressure gauge 60 is connected to the line 58. A pump 62 and a check valve 64 can be connected upstream of the pressure gauge 60, in the line 58. The fluid inlet line 58 is connected to the vessel 20 at a position 65 elevated from the level 37, preferably remote from the level 37.

To undertake the method of the invention, flow is induced through the line 58 by operation of the pump 62 to fluidize the particles 42 within the vessel 20. After the particles are fluidized, static pressure is measured by the instrument 60.

A relationship between static pressure measured by the instrument 60 and the level of particles 42 within the vessel 20 is experimental pre-established. The static pressure measured by the instrument is compared to the pre-established relationship to effectively measure the level 37 within the vessel 20.

The flow of liquid through the line 58 must be sufficient to move the individual particles upward, that is, to expand the bed of particles 42 so that the particles do not touch, or only touch lightly, i.e., are fluidized. At this point, the particles act as a fluid and the density of the particles is additive to the density of the liquid, which increases the static pressure. The difference in density is sensed by the change in pressure required by the flow through the line 58 to suspend the particles.

FIG. 1 also illustrates an automatic control of a solids pump 72 that removes particles and reduces the level 37 within the vessel 20. The solids pump 72 includes a submerged inlet 74 and a pump outlet 76. The solids pump can be a turbo pump connected to an air lift discharge pipe such as disclosed in U.S. Pat. No. 4,767,532; or pumps disclosed in U.S. Pat. Nos. 4,107,038; or 3,941,648, all herein incorporated by reference.

A pressure switch 82 is set at a predetermined static pressure that is pre-established to correlate to a maximum desired level 37 within the vessel 20. The switch 82 is signal-connected to a control 90 that is control signal-connected to the pump 72. The pump 72 can be turned on and off to maintain the level 37 within the vessel based on a pressure signal from the switch 82.

A further pressure sensor 96, arranged to measure non-fluidized static pressure at the same level 45 within the vessel 20, can be used to send a datum signal to the control 90.

The datum signal can be used to adjust the correlation of the fluidized static pressure measured by the sensor(s) 60, 82 and the determined level 37. The datum signal would be responsive to changes in liquid level 32 and liquid density, including entrained solids, within the vessel 20.

From the foregoing, it will be observed that numerous variations and modifications may be effected without departing from the spirit and scope of the invention. It is to be understood that no limitation with respect to the specific apparatus illustrated herein in tended or should be inferred. It is, of course, intended to cover by the appended claims all such modifications as fall within the scope of the claims.

What is claimed is:

1. A method of determining the level of settled particles in a vessel containing a volume of liquid defining a liquid level and a volume of particles settled in the liquid and defining a submerged level of settled particles, comprising the steps of:

fluidizing particles above a sensed position, said sensed position below the submerged level;

measuring a fluidized static pressure of the liquid after the particles are fluidized;

correlating the fluidized static pressure to a pre-established relationship between level of settled particles and fluidized static pressure to determine the level of settled particles;

wherein the step of fluidizing the particles is further defined in that fluid from said vessel above said submerged level is forced into said vessel below said submerged level to fluidize said particles; and wherein said step of fluidizing the particles is further defined in that fluid from said vessel is recirculated by pumping fluid away from a position of said vessel remote from said sensed position to an inlet position below said sensed position.

2. The method according to claim 1, comprising the further step of removing particles from said vessel when said determined level of settled particles exceeds a predetermined level.

3. The method according to claim 2, wherein said step of removing particles is further defined by the steps of:

providing a pump having a suction end beneath the level of particles; and activating said pump automatically when said submerged level of particles reaches said predetermined level.

4. A method of determining the level of settled particles in a vessel containing a volume of liquid defining a liquid level and a volume of particles settled in the liquid and defining a submerged level of settled particles, comprising the steps of:

fluidizing particles above a sensed position, said sensed position below the submerged level;

measuring a fluidized static pressure of the liquid after the particles are fluidized;

correlating the fluidized static pressure to a pre-established relationship between level of settled particles and fluidized static pressure to determine the level of settled particles; and wherein said step of correlating is further defined by the steps of (a) making a static pressure determination at a level in the vessel equal to a level of said sensed position with the particles in a settled, non fluidized state, and (b) adjusting the pre-established relationship.

5. A method of determining the level of settled particles in a vessel containing a volume of liquid defining a liquid level and a volume of particles settled in the liquid and defining a submerged level of settled particles, comprising the steps of:

fluidizing particles above a sensed position, said sensed position below the submerged level;

measuring a fluidized static pressure of the liquid after the particles are fluidized;

correlating the fluidized static pressure to a pre-established relationship between level of settled particles and fluidized static pressure to determine the level of settled particles; and wherein said step of correlating is further defined by the steps of, (a) making a continuous static pressure determination at a level in the vessel equal to a level of said sensed position with the particles in a settled, non-fluidized state, and (b) continuously adjusting the pre-established relationship.

6. The method according to claim 5, comprising the further step of removing particles from said vessel automatically when said determined level of settled particles exceeds a predetermined level.

7. The method according to claim 5, wherein said static pressure determination is made at a location in the vessel remote from said sensed position.

8. A measuring system for determining a level of settled particles in a fluid-containing vessel, comprising:

a vessel containing a quantity of fluid and a quantity of particles settled at a bottom of the vessel defining a submerged level of settled particles;

a pressure sensor arranged to sense static pressure at a sensed level below said submerged level of settled particles;

a fluidizing liquid inlet into said vessel arranged below said submerged level; and a pipe connected to said fluidizing liquid inlet, said pressure sensor comprises a pressure gauge connected to said pipe, and a liquid pump connected to said pipe and having a pump inlet connected to said vessel above said submerged level.

9. The system according to claim 8, wherein said settled particles comprises sand.

10. The system according to claim 8, wherein said fluid comprises sewage and said settled particles comprise grit.

11. A measuring system for determining a level of settled particles in a fluid-containing vessel, comprising:

a vessel containing a quantity of fluid and a quantity of particles settled at a bottom of the vessel defining a submerged level of settled particles;

a pressure sensor arranged to sense static pressure at a sensed level below said submerged level of settled particles; and a fluidizing liquid inlet into said vessel arranged below said submerged level; and wherein said pressure sensor comprises a pressure switch, and further comprising a particle pump arranged having an inlet below said submerged level and a control signal-connected to said pressure switch and to said particle pump, said control configured to activate said pump in response to a signal from said pressure switch.

12. The system according to claim 11, wherein said fluidizing liquid inlet comprises a pipe and comprising a liquid pump connected to said pipe and having a pump inlet connected to a vessel outlet located above said submerged level.

13. The system according to claim 8, wherein said fluidizing liquid inlet is connected to pressurized media.

* * * * *